(12) United States Patent
Zhang et al.

(10) Patent No.: US 12,096,959 B1
(45) Date of Patent: Sep. 24, 2024

(54) BLOOD REGURGITATION PREVENTING PUNCTURE AND GUIDANCE DEVICE WITHOUT SKIN DILATION

(71) Applicant: SHANDONG BRANDEN MEDICAL DEVICE CO., LTD, Dezhou (CN)

(72) Inventors: Haijun Zhang, Dezhou (CN); Shudi Zhi, Dezhou (CN); Kunshan Yuan, Dezhou (CN)

(73) Assignee: SHANDONG BRANDEN MEDICAL DEVICE CO. , LTD, Dezhou (CN)

( * ) Notice: Subject to any disclaimer, the term of this patent is extended or adjusted under 35 U.S.C. 154(b) by 0 days.

(21) Appl. No.: 18/616,200

(22) Filed: Mar. 26, 2024

Related U.S. Application Data

(63) Continuation of application No. PCT/CN2023/113432, filed on Aug. 17, 2023.

(30) Foreign Application Priority Data

May 6, 2023 (CN) .......................... 202310497602.1

(51) Int. Cl.
| | |
|---|---|
| *A61B 17/34* | (2006.01) |
| *A61B 34/20* | (2016.01) |
| *A61B 17/00* | (2006.01) |
| *A61B 90/00* | (2016.01) |
| *A61M 25/01* | (2006.01) |

(52) U.S. Cl.
CPC ...... *A61B 17/3496* (2013.01); *A61B 17/3423* (2013.01); *A61B 34/20* (2016.02); *A61B 2017/0023* (2013.01); *A61B 2017/0046* (2013.01); *A61B 2017/00862* (2013.01); *A61B 2090/034* (2016.02); *A61B 2090/3925* (2016.02); *A61B 2090/3966* (2016.02); *A61B 2090/3995* (2016.02); *A61M 25/0108* (2013.01)

(58) Field of Classification Search
CPC ............ A61B 17/3496; A61B 17/3423; A61B 2017/0046; A61B 2090/034; A61B 2090/3925; A61B 2090/3966; A61B 2090/3995; A61B 17/3494; A61B 17/34; A61B 17/3421; A61B 17/3417; A61B 90/00; A61B 90/03; A61B 2090/033; A61B 90/39; A61M 25/0108; A61M 29/00; A61M 25/01; A61M 25/0105
See application file for complete search history.

(56) References Cited

U.S. PATENT DOCUMENTS

2023/0149675 A1* 5/2023 Leung .................. A61M 29/02
604/164.1

FOREIGN PATENT DOCUMENTS

| CN | 201768251 U | 3/2011 |
|---|---|---|
| CN | 104800954 A | 7/2015 |
| CN | 205107826 U | 3/2016 |

(Continued)

*Primary Examiner* — Jason E Flick
(74) *Attorney, Agent, or Firm* — Bayramoglu Law Offices LLC

(57) ABSTRACT

A blood regurgitation preventing puncture and guidance device without skin dilation is provided. The puncture and guidance device mainly includes a needle tube, a dilation tube, a sheath, and a deceleration and stop device. A hydrophilic ultrasound developing coating is provided on a surface of the sheath to lay a foundation for visual puncture. The sheath and the dilation tube contain X-ray developing particles, and are provided with a transition section.

10 Claims, 8 Drawing Sheets

(56) References Cited

FOREIGN PATENT DOCUMENTS

| | | | |
|---|---|---|---|
| CN | 106377301 A | 2/2017 | |
| CN | 106725759 A | 5/2017 | |
| CN | 109965946 A | 7/2019 | |
| CN | 114870208 A | 8/2022 | |
| CN | 115920203 A | 4/2023 | |
| CN | 116196075 A | 6/2023 | |
| EP | 0413493 A2 | 2/1991 | |
| EP | 413493 B1 * | 5/1996 | ......... A61B 17/3403 |

* cited by examiner

BLOOD REGURGITATION PREVENTING PUNCTURE AND GUIDANCE DEVICE WITHOUT SKIN DILATION

CROSS-REFERENCE TO THE RELATED APPLICATIONS

This application is a continuation application of International Application No. PCT/CN2023/113432, filed on Aug. 17, 2023, which is based upon and claims priority to Chinese Patent Application No. 202310497602.1, filed on May 6, 2023, the entire contents of which are incorporated herein by reference.

TECHNICAL FIELD

The present disclosure belongs to the technical field of medical appliances, and mainly relates to a blood regurgitation preventing puncture and guidance device without skin dilation.

BACKGROUND

As a common treatment method in clinical medicine, percutaneous vascular access can be used to treat cancers and cardiovascular diseases. Seldinger technique is commonly used to assist puncture and guide a medical appliance to vessels. Compared with direct puncture, this technique is advantageous for less injury to the vessels, less bleeding, etc.

At present, the common Seldinger technique is cumbersome and roughly includes the following steps:
(1) A puncture needle is used to enter the vessel through skin, an adipose layer, a superficial fascia and a deep fascia; (2) a guidewire is delivered to the vessel through the puncture needle; (3) the puncture needle is withdrawn from the other end of the guidewire; (4) a scalpel is used for skin dilation along the guidewire to reduce the resistance of a catheter sheath during puncture; (5) the catheter sheath is inserted along the guidewire; (6) a dilation tube in catheter sheath is withdrawn; (7) a catheter is delivered to the sheath slowly and to a predetermined site in the vessel; (8) the sheath is withdrawn.

In addition to complex operation, the Seldinger technique highly depends on experiences and skills of medical workers during puncture, and is prone to vessel penetration for a beginner. Meanwhile, skin dilation before the delivery of the sheath makes patients more painful and at risk to infections. In the Seldinger technique, there is a chronological sequence for the withdrawal of the dilation tube and the delivery of the catheter, and this causes two problems: (1) after the dilation tube is withdrawn, blood flows out quickly along the sheath under a venous pressure. For this inevitable process, it is a common practice for the medical workers to press the vessel with a hand to reduce bleeding; (2) in step (7), a part of air in the catheter sheath is pushed to the vessel with entry of the catheter. This causes a sharp increase of gas in the blood and a discomfort of the patient.

In 2015, the patent CN106377301A provides a vessel puncture outfit. According to the device, through an interference fit portion and a transition portion, no gap is generated when the catheter sheath is bent. This solves a projecting or folding problem during vessel puncture, makes the catheter sheath inserted into the vessel more smoothly, reduces a resistance, and effectively prevents injury to the vessel. However, whether skin dilation is carried out during the puncture is not described in the patent. Since all catheter sheaths used in clinical practices are subjected to the skin dilation, it can be considered that the skin dilation is carried out in the patent to achieve the smoother insertion process. In addition, the interference fit portion and the transition portion in the vessel puncture outfit have a total length of 20-37 mm, while the interference fit portion and the transition portion in a dilator have a length of 15-25 mm. With a cephalic vein of an adult (which is a common puncture vessel in peripheral puncture) for example, the vessel has a diameter of 6-10 mm. In response to puncture at an angle of 30° with a human body, the vessel is penetrated easily to cause a puncture failure. The patent CN114870208A provides an intubation device integrated with a catheter, a guidewire and a puncture needle. A coarse needle is directly used to puncture the vessel. In spite of a simple process, the operation causes a large trauma to the vessel and is prone to massive prolonged bleeding. The patent CN104800954A provides a valve-adjustable catheter sheath. The catheter sheath is provided with two hemostasis valves at a proximal end. The first hemostasis valve has a small opening size and is made of a deformation-resistant material. The second hemostasis valve has a large opening size and is made of a deformable material. The catheter sheath is applied to guide and insert a fine catheter, and can effectively prevent blood regurgitation caused by a large gap between the sheath and the catheter. However, it is obvious that the catheter sheath is not suitable for a catheter having a similar inner diameter as the catheter sheath. Although the second hemostasis valve can be adjusted in opening size to reduce a force of friction, the catheter is hardly inserted due to an overlarge elastic modulus of the first hemostasis valve. In addition, for a vascular access catheter, in order to reduce thrombosis and ensure an infusion speed, a diameter of the catheter is generally ⅓ of a diameter of the vessel. In case of a catheter sheath over-larger than the catheter, serious injury to the vessel is caused in insertion. Therefore, this device is not suitable for the vascular access catheter in puncture and catheter guidance.

SUMMARY

The present disclosure provides a puncture and guidance device to solve the above problem. With a valve, the puncture and guidance device does not require skin dilation and can prevent blood regurgitation. Through material selection and structural size design of a sheath and a dilation tube, the present disclosure can effectively reduce a puncture resistance from a skin, a tissue and a vessel. A valve structure in the sheath prevents the blood regurgitation or reduces an amount of air to enter the vessel. The device not only has X-ray and ultrasound dual developing functions, but also prevents vessel penetration. After entering the vessel during percutaneous tissue puncture, the present disclosure can give a bloodline prompt to a medical worker and assist a deceleration and stop function.

The present disclosure adopts the following technical solutions.

A blood regurgitation preventing puncture and guidance device without skin dilation includes a needle tube, a dilation tube, a sheath, a deceleration and stop device, and a handle, where the needle tube has an outer diameter of 0.5-2.2 mm, and both the sheath and the dilation tube contain X-ray developing particles.

Further, the dilation tube includes a connecting seat, a main body section, and a transition section; an inner diameter of the main body section of the dilation tube matches with the needle tube and is 0.03-0.08 mm greater than the outer diameter of the needle tube; the main body section of the dilation tube has a wall thickness of 0.05-1 mm and an axial length of 52-78 mm; the transition section of the dilation tube is connected to the main body section of the dilation tube, and is a tapered structure; along an axial direction of the dilation tube away from the main body section of the dilation tube, an inner diameter, an outer diameter and a wall thickness of the transition section of the dilation tube decrease gradually; the transition section of the dilation tube has an axial length of 8-12 mm; a minimum inner diameter of the transition section of the dilation tube is 0.03-0.08 mm less than the outer diameter of the needle tube; and a position with the minimum inner diameter on the transition section of the dilation tube has a wall thickness of 0.04-0.12 mm.

Further, the sheath includes a transition section, a valve, a main body section, a hydrophilic ultrasound developing coating, and a seat; the transition section of the sheath is connected to the main body section of the sheath, and is a tapered structure; along an axial direction of the sheath away from the main body section of the sheath, an inner diameter, an outer diameter and a wall thickness of the transition section of the sheath decrease gradually; the transition section of the sheath has an axial length $L_2$ of 3-5 mm; a minimum inner diameter of the transition section of the sheath is 0.03-0.08 mm less than an outer diameter of the main body section of the dilation tube; a position with the minimum inner diameter on the transition section of the sheath has a wall thickness of 0.02-0.08 mm; and the main body section of the sheath has an axial length $L_1$ of 30-75 mm, and a wall thickness of 0.05-0.8 mm.

Further, the deceleration and stop device includes a dilation tube hole, a connecting post, a housing, two spring holes, two first springs, two spring pin holes, a first spring pin, a second spring pin, two grooves, a push plunger, a disposable fixture member, a spring fixture member, a sliding barrel, a sleeving rod, a fixed hoop, a support rod, a distraction rod, and a second spring; the connecting post is in threaded connection with the seat of the sheath; the dilation tube hole and the two spring pin holes are sequentially formed in the connecting post; the push plunger is provided with the two grooves, the two spring holes, and holes respectively matching with the disposable fixture member and the spring fixture member; the spring holes are close to an edge of the push plunger, and respectively communicate with the grooves, with a diameter greater than a diameter of the groove; the groove, the spring hole and the spring pin hole at a same side are coaxial; the first springs are respectively sleeved on the first spring pin and the second spring pin, and are in a natural state; the first spring includes one end connected to the spring hole, and the other end connected to the connecting post; the first spring pin and the second spring pin each include one end fixedly connected to the spring pin hole, and the other end exposed out of the spring pin hole and contacting the groove; the disposable fixture member and the spring fixture member each are an elongated structure with bumps at two ends; the disposable fixture member and the spring fixture member each are connected to the handle, and include one end located in the groove and the other end located in the sliding barrel; the sliding barrel is sleeved on the sleeving rod, and axially and slidably connected to the sleeving rod; the sleeving rod is sequentially in threaded connection with the push plunger and the connecting seat of the dilation tube; the fixed hoop is fixed outside a top of the sleeving rod; the sliding barrel is connected to the fixed hoop through the second spring; the second spring is in an extended state; and the sliding barrel and the support rod, the fixed hoop and the distraction rod, as well as the distraction rod and the support rod are rotatably connected to each other.

Further, the handle penetrates through the sleeving rod, and is in threaded connection with the sleeving rod and the connecting seat of the dilation tube.

Further, the needle tube and the dilation tube are integrated by injection molding; a head end of the needle tube is exposed out of the transition section of the dilation tube; the dilation tube and the needle tube axially penetrate through the sheath; and the transition section of the dilation tube is entirely exposed out of the sheath.

Further, the dilation tube is made of a high polymer material with a certain hardness, and the high polymer material may be one or more selected from the group consisting of polypropylene (PP), high density polyethylene (HDPE), polycarbonate (PC), polyether-ether-ketone (PEEK), polystyrene (PS) and polyamide (PA).

Further, an outer contour of the transition section of the dilation tube is tangent to an outer contour of the main body section of the dilation tube.

Further, the main body section and the transition section of the sheath are made of an elastic and rigid high polymer material, and the high polymer material may be one or more selected from the group consisting of polytetrafluoroethylene (PTFE), a tetrafluoroethylene-ethylene copolymer, a tetrafluoroethylene-hexafluoropropylene copolymer, a chlorotrifluoroethylene-propylene copolymer, polyurethane (PU), polyvinyl chloride (PVC) and a thermoplastic elastomer (TPE).

Preferably, the main body section of the sheath has the axial length $L_1$ of 30-50 mm; the main body section of the sheath has an inner diameter of 1.2-2.5 mm; and the inner diameter of the main body section of the sheath is 0.05-0.1 mm greater than an outer diameter of the dilation tube.

Preferably, an outer contour of the transition section of the sheath is tangent to an outer contour of the main body section of the sheath. After the dilation tube is inserted into the sheath, the transition section of the sheath is tightly attached to an outer surface of the main body section of the dilation tube. With a certain elasticity, the transition section of the sheath does not cause a crack at an edge.

Further, the valve is located in the transition section of the sheath and close to the main body section of the sheath; the valve is made of a material with an elastic modulus of less than 3 MPa; the valve is an elastic membrane with one or more notches; a diameter of the elastic membrane falls between a diameter of the main body section of the sheath and a diameter of the main body section of the dilation tube; the notch passes through a center of the elastic membrane; and a size of the notch falls between the diameter of the elastic membrane and the diameter of the main body section of the dilation tube. After the dilation tube is withdrawn from the sheath, the notch of the valve is closed to prevent blood regurgitation. When a catheter is guided for intervention, air in the main body section of the sheath is prevented from entering a vessel with the catheter to cause air embolism.

Preferably, an easy tear line is provided on a surface of the sheath and perpendicular to the notch of the valve; and the easy tear line is located on a same axial section as the notch, and may be integrally formed with the sheath by co-extrusion.

Further, the X-ray developing particles are made of one selected from the group consisting of barium sulfate, metal tungsten, metal tantalum and a bismuth-containing compound; the bismuth-containing compound may be bismuth oxide; and the X-ray developing particles have a size of 1-50 μm.

Further, the hydrophilic ultrasound developing coating mainly includes a hydrophilic polymer and metal particles.

Preferably, in the hydrophilic ultrasound developing coating, the metal particles are alloy particles or pure metal particles; and preferably, the metal particles have a size of 1-50 μm.

Preferably, in the hydrophilic ultrasound developing coating, the hydrophilic polymer is one or more selected from the group consisting of polyvinylpyrrolidone (PVP), polyethylene glycol (PEG), polyvinyl alcohol, polyacrylic acid and polyacrylamide.

Optionally, the housing of the deceleration and stop device is divided into an upper portion and a lower portion along an axial direction of the handle, and the upper portion and the lower portion are connected and fixed through a fastener.

Further, the dilation tube is provided in the dilation tube hole of the deceleration and stop device.

Further, the end of each of the first spring pin and the second spring pin that is exposed out of the spring pin hole is an oblique surface; and an inclination angle of the oblique surface of the first spring pin is greater than an inclination angle of the oblique surface of the second spring pin.

Further, the push plunger includes one end being truncated cone shaped, and the other end being cylindrical; the truncated cone shaped end is close to the sliding barrel; the grooves are located in the cylindrical portion; and the grooves respectively match with the first spring pin and the second spring pin in size and shape.

Optionally, the spring holes are symmetrically distributed in the push plunger.

Further, the sleeving rod is a cylindrical structure provided with an axial gap and having one end sealed; the bump at one end of each of the disposable fixture member and the spring fixture member enters the groove through the gap of the sleeving rod; the bump at the other end of the disposable fixture member enters the sliding barrel through the gap; and the bump at the other end of the spring fixture member is flush with an outer surface of the sleeving rod through the gap of the sleeving rod.

Further, the disposable fixture member is unidirectionally and slidably connected to the handle; there is a certain gap between an elongated portion of the disposable fixture member and the handle; the bump of the disposable fixture member entering the groove matches with the second spring pin in shape; when the second spring pin enters the corresponding groove, the second spring pin squeezes the disposable fixture member, such that the whole disposable fixture member moves radially relative to the sleeving rod, and the bumps at the two ends of the disposable fixture member enter the push plunger; two ends of the spring fixture member are connected to the handle through a spring; the spring is in a natural state; a middle of the spring fixture member is rotatably connected to the handle through a strut; there is a certain gap between the spring fixture member and the handle; the bump of the spring fixture member entering the groove matches with the first spring pin in shape; when the first spring pin enters the corresponding groove, the spring fixture member is squeezed, with a contacting end moving radially toward the sleeving rod; and under a support force of the strut, the whole spring fixture member rotates, with the other end protruding from the outer surface of the sleeving rod.

Further, the disposable fixture member and the spring fixture member are opposite around the handle, and are coaxial (a centerline of the disposable fixture member and a centerline the spring fixture member are perpendicular to an axis of the handle); a height of the bump of the disposable fixture member entering the groove and a height of the bump of the spring fixture member entering the groove are respectively less than a width of the first spring pin and a width of the second spring pin; and an axial length of the spring fixture member is greater than an axial length of the disposable fixture member.

Further, the strut is deviated from the middle of the spring fixture member, and close to the one end of the spring fixture member with the bump entering the groove, such that when one end of the spring fixture member in the groove is squeezed, the other end of the spring fixture member may have a large displacement.

Optionally, the sliding barrel is connected to the sleeving rod through a sliding track; and the sliding barrel and the support rod, the fixed hoop and the distraction rod, and the distraction rod and the support rod are hinged to each other.

Further, there may be two or more support rods and two or more distraction rods, and the support rods and the distraction rods have the same number.

Before puncture, the first spring is in the natural state, the second spring is in the extended state, the sliding barrel is fixed by the disposable fixture member, and both the support rod and the distraction rod are collapsed. During the puncture, the first spring is in a compressed state, the disposable fixture member is withdrawn from the groove, the sliding barrel is fixed by the spring fixture member, and the second spring keeps the extended state. When the transition section of the sheath penetrates through a vessel, a puncture resistance decreases, the first spring is restored to the natural state, the spring fixture member is restored to a position axially parallel to the sleeving rod, the second spring is compressed to drive the sliding barrel to move toward the fixed hoop along the sleeving rod, and the support rod and the distraction rod are expanded.

The device provided by the present disclosure is integrated with puncture and guidance. With an axially rigid and smooth transition structure, not only can the operating steps be reduced, but also no skin expansion is required in use. The elastic valve in the outer sheath of the device reduces blood regurgitation and air embolism. With the hydrophilic ultrasound developing coating outside the sheath, after the sheath enters the vessel, blood rises a certain distance along the coating, so as to indicate a medical worker of the distance of the device in the vessel. On the other hand, with the deceleration and stop device at the handle of the device, after the transition section of the outer sheath also enters the vessel, the puncture resistance decreases sharply, and the distraction rod in the deceleration and stop device is expanded. This helps the medical worker decrease a force, so as not to puncture the vessel mistakenly during the puncture.

The present disclosure has the following beneficial effects:

1. Through material selection and structural design, the present disclosure first provides the blood regurgitation preventing puncture and guidance device without skin dilation. Skin dilation is carried out during puncture, and there is no need to use a guidewire to guide the sheath for puncture. This reduces operating steps in catheterization, and reduces injury to a patient.

2. With the device provided by the present disclosure, there is no need to carry out the skin dilation in catheterization. Compared with a conventional sheathed puncture needle, an effective length of the device is more suitable for a tissue structure of a human body. The device does not cause a puncture failure due to obesity of the patient, and has a wider application range and less injury to the vessel of the patient.

3. The present disclosure provides the valve structure to prevent the blood regurgitation and the air embolism. When the dilation tube is withdrawn from the sheath, the valve is closed, and the blood cannot flow out along an inner wall of the sheath. When the catheter enters the main body section of the sheath, the valve keeps closed to reduce air entering the vessel. When the catheter enters the valve of the sheath, the catheter with the guidewire can easily cause deformation of the low-elastic-modulus valve. The catheter sequentially enters the transition section and the vessel. This can effectively reduce an occurrence rate of related adverse events.

4. The present disclosure provides the deceleration and stop device to assist the puncture. Before the transition section of the sheath enters the vessel, the support rod and the distraction rod in the deceleration and stop device are collapsed, and the medical worker can hold the deceleration and stop device for the puncture. When the transition section of the sheath enters the vessel, the support rod and the distraction rod are expanded, such that a hand of the medical worker is stressed and separated, and a prompt on a puncture site is given to the medical worker. Thereafter, the medical worker can hold the handle to adjust a puncture angle to continuously carry out the puncture in the vessel. This reduces unnecessary injury to the vessel due to an improper puncture force.

5. With the hydrophilic ultrasound developing coating on the surface of the sheath, the present disclosure can cooperate with ultrasound guided puncture. On the other hand, after the sheath enters the blood, the blood rises a certain distance along the coating to give a visual prompt to the medical worker.

6. Both the sheath and the dilation tube contain the X-ray developing particles, so the present disclosure can cooperate with X-ray guided puncture. The sheath and the dilation tube can resist a high pressure and prevent leakage of a developing agent, so the present disclosure is applied to repeated puncture, and quick infusion of the developing agent at a high pressure in contrast examination of a diabetic patient with a poor superficial vessel condition. The present disclosure is further applied to superficial vein puncture with a desirable developing effect and no leakage of the developing agent.

In the figures: 1: needle tube, 2: dilation tube, 3: sheath, 3.1: transition section, 3.2: valve, 3.3: main body section, 3.4: hydrophilic ultrasound developing coating, 3.5: metal particle, 3.6: X-ray developing particle, 3.7: seat, 4: deceleration and stop device, 4.1: dilation tube hole, 4.2: connecting post, 4.3: housing, 4.4: spring hole, 4.5: first spring, 4.6: spring pin hole, 4.7: first spring pin, 4.8: second spring pin, 4.9: groove, 4.10: push plunger, 4.11: disposable fixture member, 4.12: spring fixture member, 4.13: sliding barrel, 4.14: sleeving rod, 4.15: fixed hoop, 4.16: support rod, 4.17: distraction rod, 4.18: second spring, 5: handle, $L_1$: axial length of the main body section of the sheath, and $L_2$: axial length of the transition section of the sheath.

DETAILED DESCRIPTION OF THE EMBODIMENTS

In order to make the objectives, technical solutions, and advantages of the present disclosure clearer, the present disclosure is further described in detail below with reference to FIGS. 1-9 and embodiments. It should be noted that the drawings are simplified and do not use an accurate proportion, that is, the drawings are only for the objectives of conveniently and clearly assisting in illustrating embodiments of the present disclosure. It should be understood that the specific embodiments described herein are merely intended to explain the present disclosure, rather than to limit the present disclosure. All other embodiments obtained by persons of ordinary skill in the art based on the embodiments of the present disclosure without creative efforts should fall within the protection scope of the present disclosure.

Embodiment 1

Figure 1:
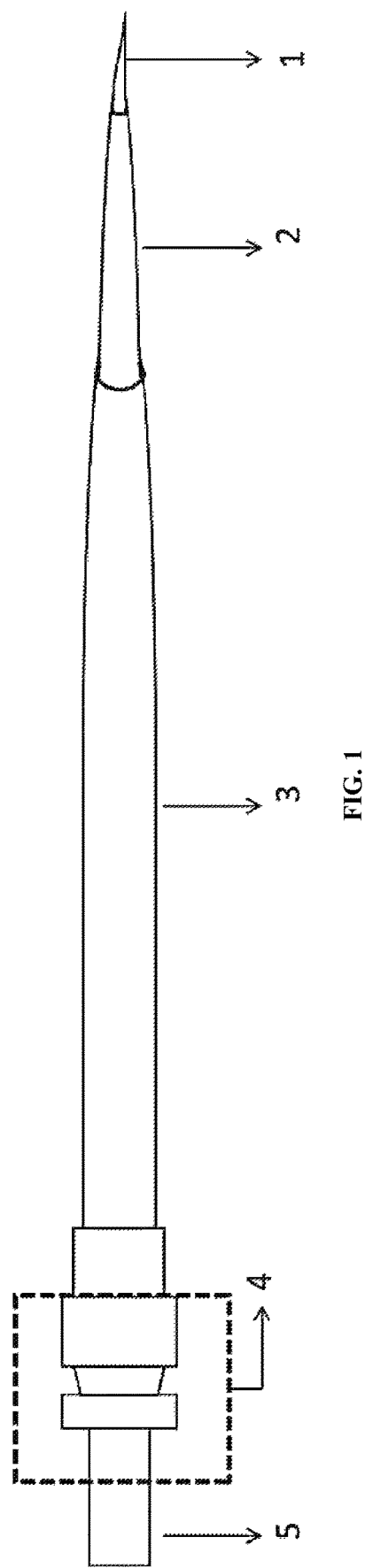
FIG. 1 is a schematic structural view of a blood regurgitation preventing puncture and guidance device without skin dilation according to the present disclosure.
Figure 2:
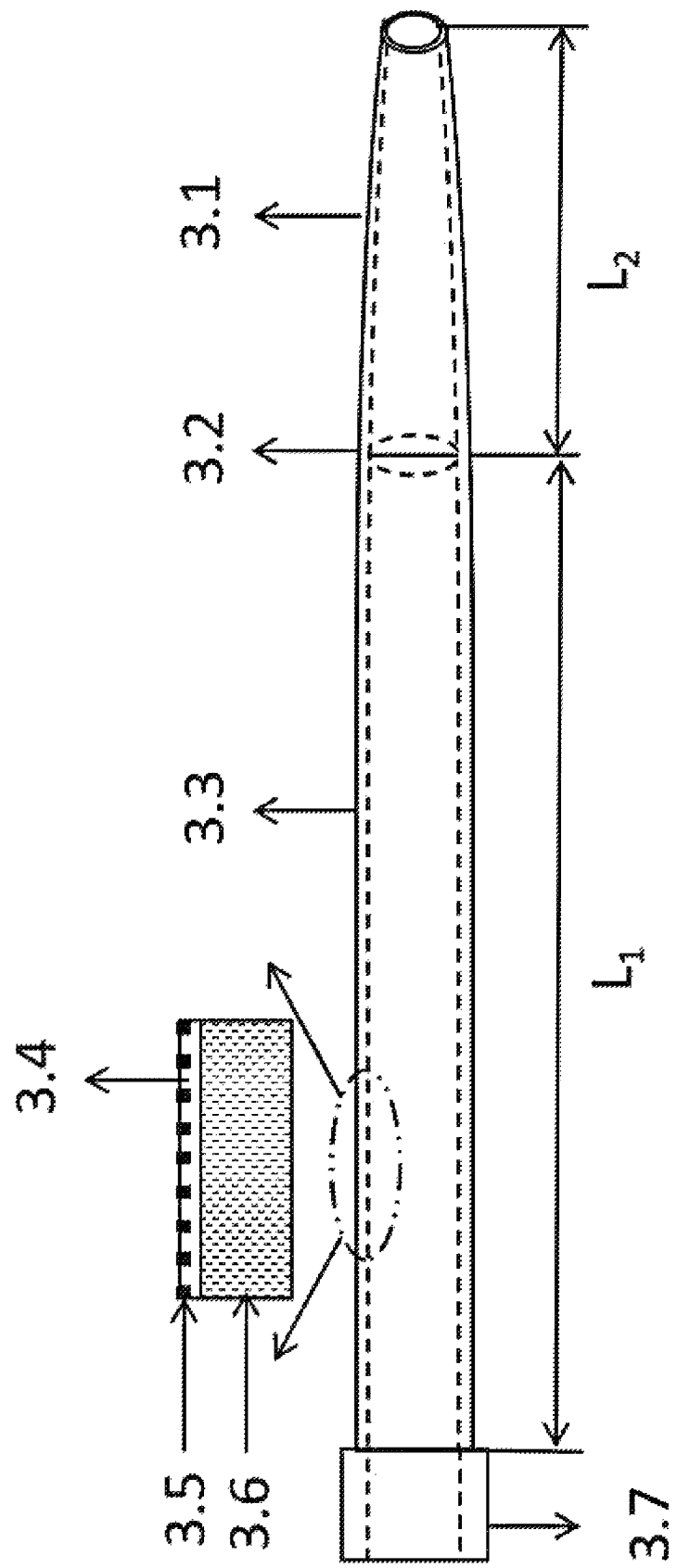
FIG. 2 is a schematic structural view of a sheath.

As shown in FIG. 1 to FIG. 2, a blood regurgitation preventing puncture and guidance device without skin dilation includes needle tube 1, dilation tube 2, sheath 3, deceleration and stop device 4, and handle 5. Both the sheath 3 and the dilation tube 2 contain X-ray developing particles 3.6.

Further, the dilation tube 2 includes a connecting seat, a main body section, and a transition section. An inner diameter of the main body section of the dilation tube 2 matches with the needle tube 1 and is 0.03-0.08 mm greater than the outer diameter of the needle tube 1. The main body section of the dilation tube has a wall thickness of 0.05-1 mm and an axial length of 52-78 mm. The transition section of the dilation tube 2 is connected to the main body section of the dilation tube 2, and is a tapered structure. Along an axial direction away from the main body section of the dilation tube 2, an inner diameter, an outer diameter and a wall thickness of the transition section of the dilation tube 2 decrease gradually. The transition section of the dilation tube 2 has an axial length of 8-12 mm. A minimum inner diameter of the transition section of the dilation tube 2 is 0.03-0.08 mm less than the outer diameter of the needle tube 1. A position with the minimum inner diameter on the transition section of the dilation tube has a wall thickness of 0.04-0.12 mm.

Further, the dilation tube 2 is made of a high polymer material with a certain hardness that may be one or more selected from the group consisting of PP, HDPE, PC, PEEK, PS and PA. An outer contour of the transition section of the dilation tube 2 is tangent to an outer contour of the main body section of the dilation tube 2.

Further, the needle tube 1 has the outer diameter of 0.5-2.2 mm, and is integrated with the dilation tube 2 by injection molding. A head end of the needle tube 1 is exposed out of the transition section of the dilation tube 2.

Further, the sheath 3 includes transition section 3.1 of the sheath 3, valve 3.2, main body section 3.3 of the sheath 3, hydrophilic ultrasound developing coating 3.4, and seat 3.7. The transition section 3.1 of the sheath 3 is connected to the main body section 3.3 of the sheath 3, and is a tapered structure. Along an axial direction away from the main body section 3.3 of the sheath 3, an inner diameter, an outer diameter and a wall thickness of the transition section 3.1 of the sheath 3 decrease gradually. The transition section 3.1 of the sheath 3 has an axial length $L_2$ of 3-5 mm. A minimum inner diameter of the transition section 3.1 of the sheath 3 is 0.03-0.08 mm less than an outer diameter of the main body section of the dilation tube 2. A position with the minimum inner diameter on the transition section of the sheath has a wall thickness of 0.02-0.08 mm. The main body section 3.3 of the sheath 3 has an axial length $L_1$ of 30-75 mm, and a wall thickness of 0.05-0.8 mm.

Further, the main body section 3.3 and the transition section 3.1 of the sheath 3 are made of an elastic and rigid high polymer material that may be one or more selected from the group consisting of PTFE, a tetrafluoroethylene-ethylene copolymer, a tetrafluoroethylene-hexafluoropropylene copolymer, a chlorotrifluoroethylene-propylene, PU, PVC and a TPE.

Preferably, the main body section 3.3 of the sheath 3 has the axial length $L_1$ of 30-50 mm and an inner diameter of 1.2-2.5 mm, and is 0.05-0.1 mm greater than the outer diameter of the main body section of the dilation tube 2. An outer contour of the transition section 3.1 of the sheath 3 is tangent to an outer contour of the main body section 3.3 of the sheath 3. After the dilation tube 2 is inserted into the sheath 3, the transition section 3.1 of the sheath 3 is tightly attached to an outer surface of the main body section of the dilation tube 2. With a certain elasticity, the transition section 3.1 does not cause a crack at an edge.

As can be seen from FIG. 2, the valve 3.2 is located in the transition section 3.1 of the sheath 3 and close to the main body section 3.3 of the sheath 3. In the present disclosure, the valve 3.2 is made of a material with an elastic modulus of less than 3 MPa. The valve is an elastic membrane with one or more notches. A diameter of the elastic membrane falls between a diameter of the main body section 3.3 of the sheath 3 and a diameter of the main body section of the dilation tube 2. The notch passes through a center of the elastic membrane. A size of the notch falls between the diameter of the elastic membrane and the diameter of the main body section of the dilation tube 2. After the dilation tube 2 is withdrawn from the sheath 3, the notch of the valve 3.2 is closed to prevent blood regurgitation. When a catheter is guided for intervention, air in the main body section 3.3 of the sheath 3 is prevented from entering a vessel with the catheter to cause air embolism.

Optionally, the elastic membrane is made of a silica gel, PU and a TPE, with a thickness of not greater than 0.6 mm. The notch may be one of a "line" shape, a "crisscross" shape and a "double-cross" shape. The elastic membrane is formed and notched, and then fixed on the sheath 3 by bonding.

Preferably, an easy tear line is provided on a surface of the sheath 3. The easy tear line is located on a same axial section as the notch of the valve 3.2, and may be integrally formed with the sheath 3 by co-extrusion.

In the present disclosure, the X-ray developing particles 3.6 are made of one selected from the group consisting of barium sulfate, metal tungsten, metal tantalum and a bismuth-containing compound. The X-ray developing particles 3.6 have a size of 1-50 μm. The hydrophilic ultrasound developing coating 3.4 mainly includes a hydrophilic polymer and metal particles 3.5. The metal particles 3.5 are alloy particles or pure metal particles. Preferably, the metal particles 3.5 have a size of 1-50 μm. The hydrophilic polymer may be one or more selected from the group consisting of PVP, PEG, polyvinyl alcohol, polyacrylic acid or polyacrylamide.

As shown in FIGS. 3-9, the deceleration and stop device 4 includes dilation tube hole 4.1, connecting post 4.2, housing 4.3, spring holes 4.4, first springs 4.5, spring pin holes 4.6, first spring pin 4.7, second spring pin 4.8, grooves 4.9, push plunger 4.10, disposable fixture member 4.11, spring fixture member 4.12, sliding barrel 4.13, sleeving rod 4.14, fixed hoop 4.15, support rod 4.16, distraction rod 4.17, and second spring 4.18.

Figure 3:
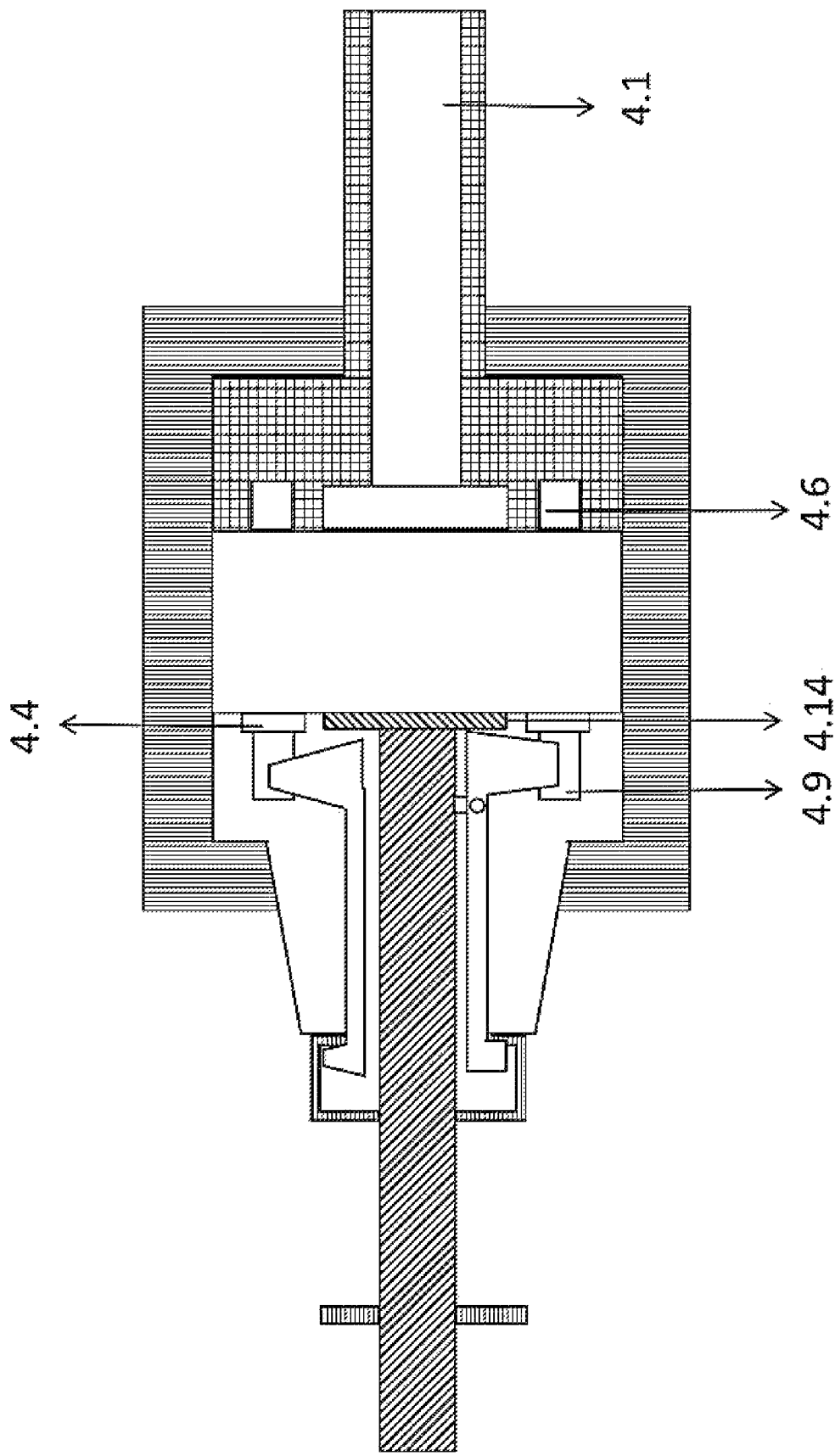
FIG. 3 is a schematic structural view of a deceleration and stop device.

As shown in FIG. 3, the dilation tube hole 4.1 and two spring pin holes 4.6 are sequentially formed in the connecting post 4.2. The push plunger 4.10 is provided with the grooves 4.9, the spring holes 4.4, and holes respectively matching with the disposable fixture member 4.11 and the spring fixture member 4.12. The spring holes 4.4 are close to an edge of the push plunger 4.10, and respectively communicate with the grooves 4.9, with a diameter greater than a diameter of the groove 4.9. The groove 4.9, the spring hole 4.4 and the spring pin hole 4.6 at a same side are coaxial.

Further, there are two spring holes 4.4, two first springs 4.5 and two grooves 4.9, and the spring holes 4.4, the first springs 4.5 and the grooves 4.9 have the same number. The connecting post 4.2 is in threaded connection with the seat 3.7 of the sheath 3.

Figure 4:
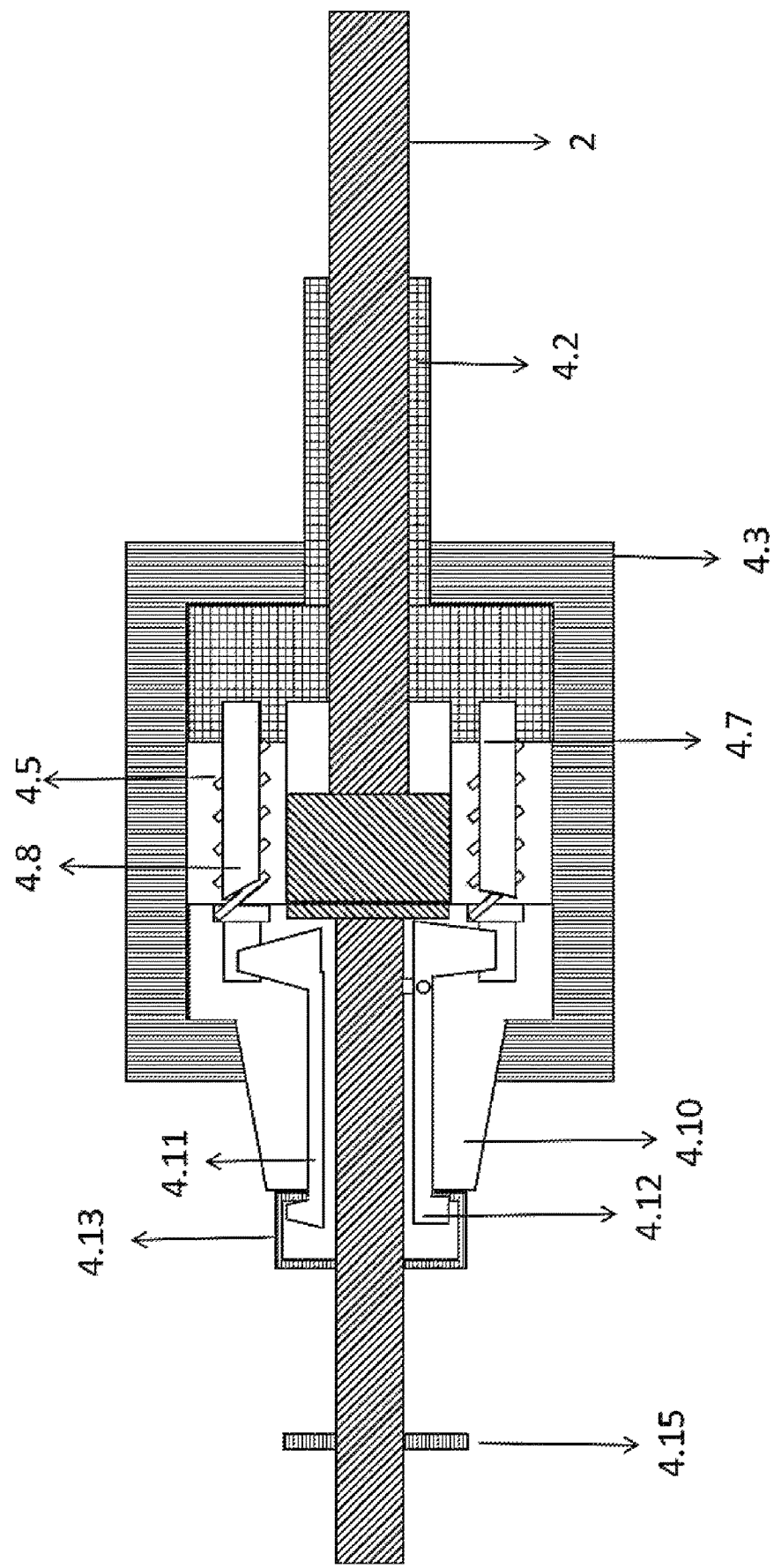
FIG. 4 is a schematic assembly view of a deceleration and stop device.
Figure 5:
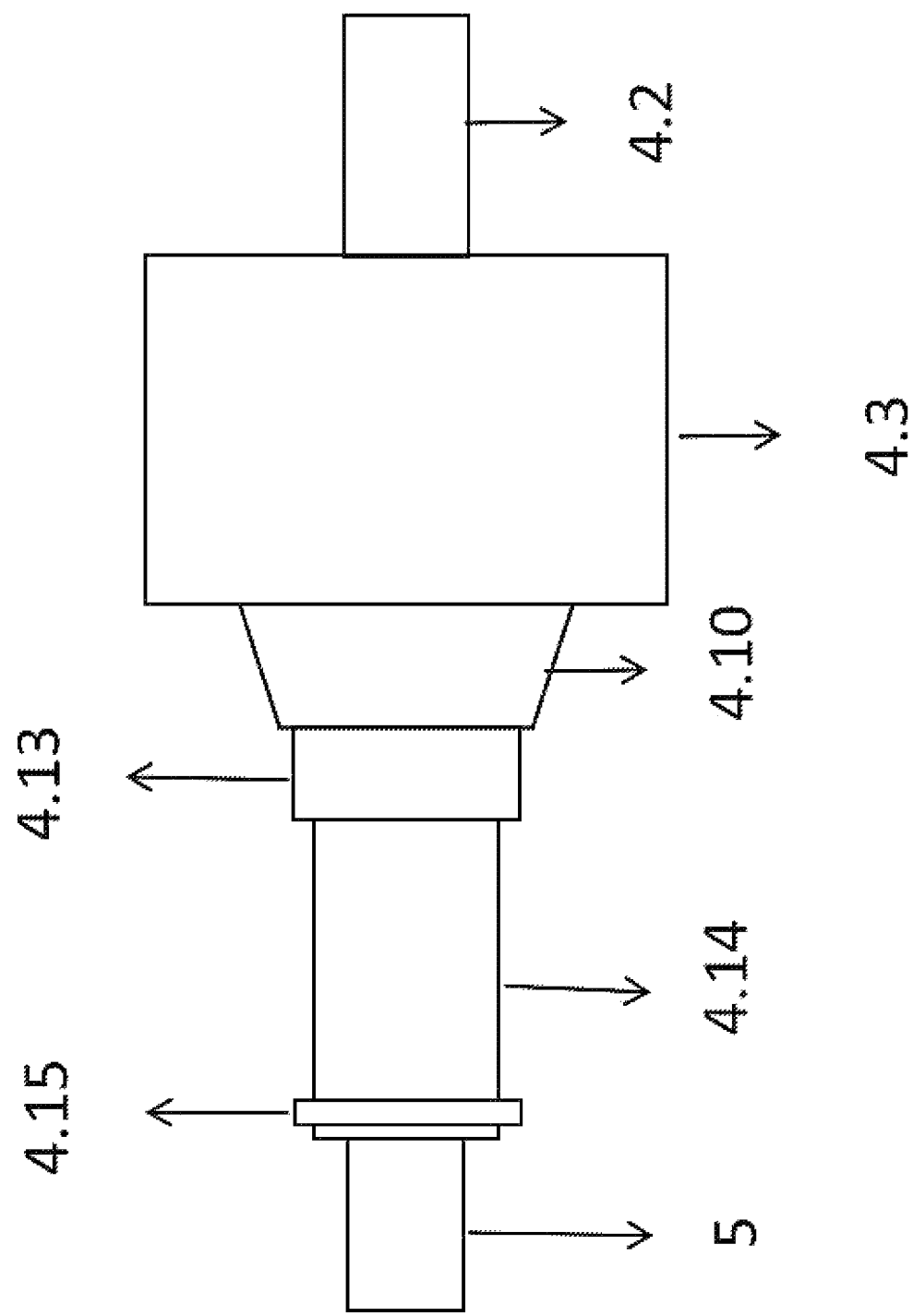
FIG. 5 is a front view of a deceleration and stop device.
Figure 6:
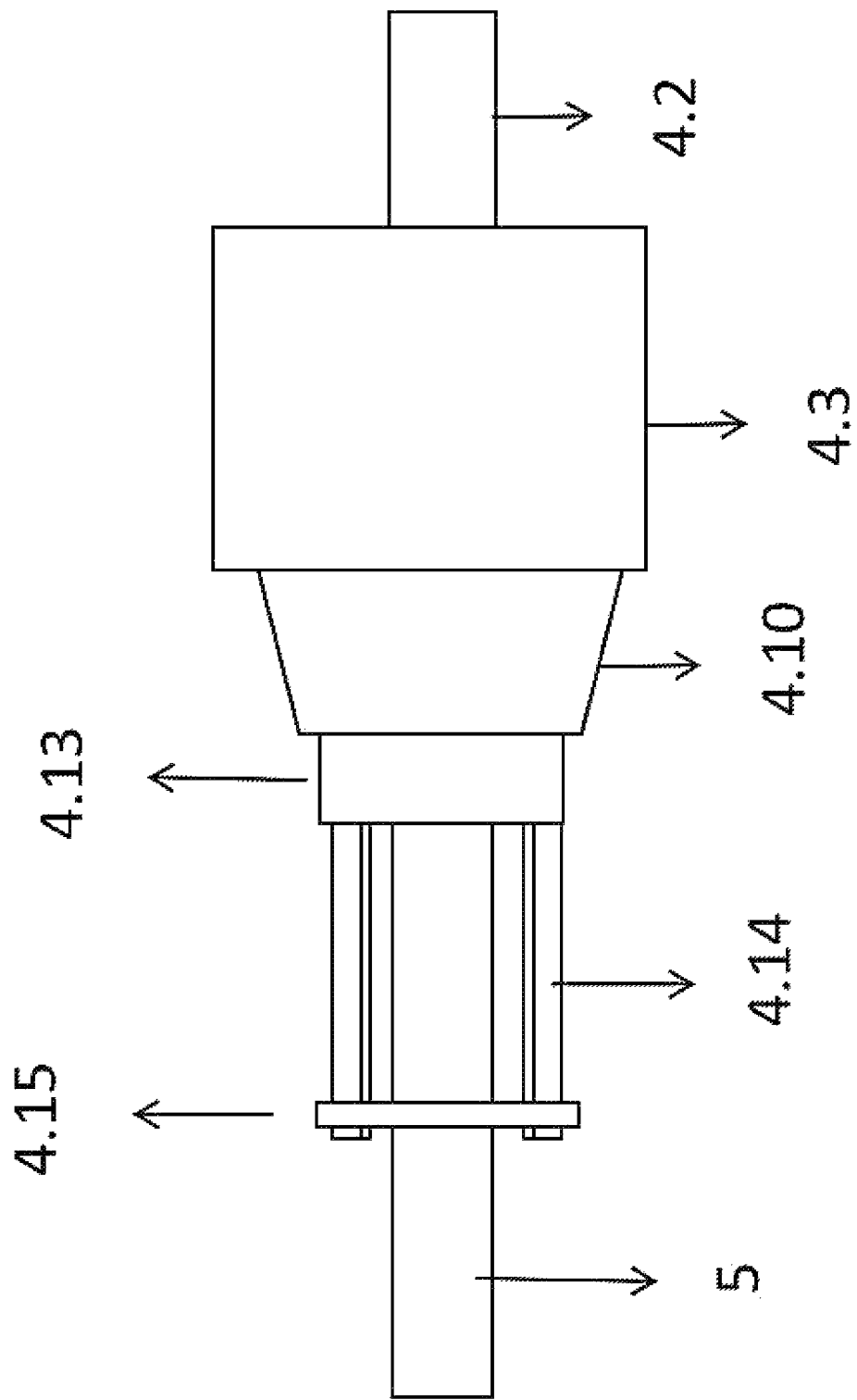
FIG. 6 is a top view of a deceleration and stop device.

As shown in FIGS. 4-6, the dilation tube 2 is provided in the dilation tube hole 4.1. The connecting seat is provided at an end close to the push plunger 4.10. The main body section of the dilation tube 2 includes a portion close to the connecting seat provided in the dilation tube hole 4.1, and a portion close to the transition section of the dilation tube 2 exposed out of the connecting post 4.2. The push plunger 4.10 includes one end being truncated cone shaped, and the other end being cylindrical. The truncated cone shaped end is close to the sliding barrel. The grooves 4.9 are located in the cylindrical portion. The grooves respectively match with the first spring pin 4.7 and the second spring pin 4.8 in size and shape. There are two first springs 4.5 that are respectively sleeved on the first spring pin 4.7 and the second spring pin 4.8. The first spring includes one end connected to the push plunger 4.10, and the other end connected to the connecting post 4.2. The first spring pin 4.7 and the second spring pin 4.8 each include one end fixedly connected to the spring pin hole 4.6, and the other end exposed out of the spring pin hole 4.6 and contacting the groove 4.9. The disposable fixture member 4.11 and the spring fixture member 4.12 each are an elongated structure with bumps at two ends. The disposable fixture member 4.11 and the spring fixture member 4.12 are connected to the handle 5. The disposable fixture member 4.11 and the spring fixture member 4.12 each include one end located in the groove 4.9, and the other end located in the sliding barrel 4.13. The sliding barrel 4.13 is sleeved on the sleeving rod 4.14, and axially and slidably connected to the sleeving rod 4.14. The sleeving rod 4.14 is sequentially in threaded connection with the push plunger 4.10 and the connecting seat. The fixed hoop 4.15 is fixed outside a top of the sleeving rod 4.14. The handle 5 penetrates through the sleeving rod 4.14. The handle 5 is in threaded connection with the sleeving rod 4.14 and the connecting seat. The end of each of the first spring pin 4.7 and the second spring pin 4.8 that is exposed out of the spring pin hole 4.6 is an oblique surface. An inclination angle of the oblique surface of the first spring pin 4.7 is greater than an inclination angle of the oblique surface of the second spring pin 4.8.

Further, the disposable fixture member 4.11 is slidably connected to the handle 5. There is a certain gap between an elongated portion of the disposable fixture member 4.11 and the handle 5. The bump of the disposable fixture member 4.11 entering the groove 4.9 matches with the second spring pin 4.8 in shape. When the second spring pin 4.8 enters the corresponding groove 4.9, the second spring pin 4.8 squeezes the disposable fixture member 4.11, such that the whole disposable fixture member 4.11 moves radially relative to the sleeving rod 4.14, and the bumps at the two ends of the disposable fixture member enter the push plunger 4.10. Two ends of the spring fixture member 4.12 are connected to the handle 5 through a spring. The spring is in a natural state. A middle of the spring fixture member 4.12 is rotatably connected to the handle 5 through a strut. There is a certain gap between the spring fixture member 4.12 and the handle 5. The bump of the spring fixture member 4.12 entering the groove 4.9 matches with the first spring pin 4.7 in shape. When the first spring pin 4.7 enters the corresponding groove 4.9, the spring fixture member 4.12 is squeezed, with a contacting end moving radially toward the sleeving rod 4.14. Under a support force of the strut, the whole spring fixture member 4.12 rotates, with the other end protruding from an outer surface of the sleeving rod 4.14.

Further, the disposable fixture member 4.11 and the spring fixture member 4.12 are opposite around the handle, and are coaxial. A height of the bump of the disposable fixture member entering the groove 4.9 and a height of the bump of the spring fixture member entering the groove are respectively less than a width of the first spring pin 4.7 and a width of the second spring pin 4.8. An axial length of the spring fixture member 4.12 is greater than an axial length of the disposable fixture member 4.11.

Further, the strut is deviated from the middle of the spring fixture member 4.12, and close to the one end of the spring fixture member 4.12 with the bump entering the groove 4.9. Under an action of the strut, when one end of the spring fixture member 4.12 in the groove 4.9 is squeezed, the other end of the spring fixture member may have a large displacement.

Figure 7:
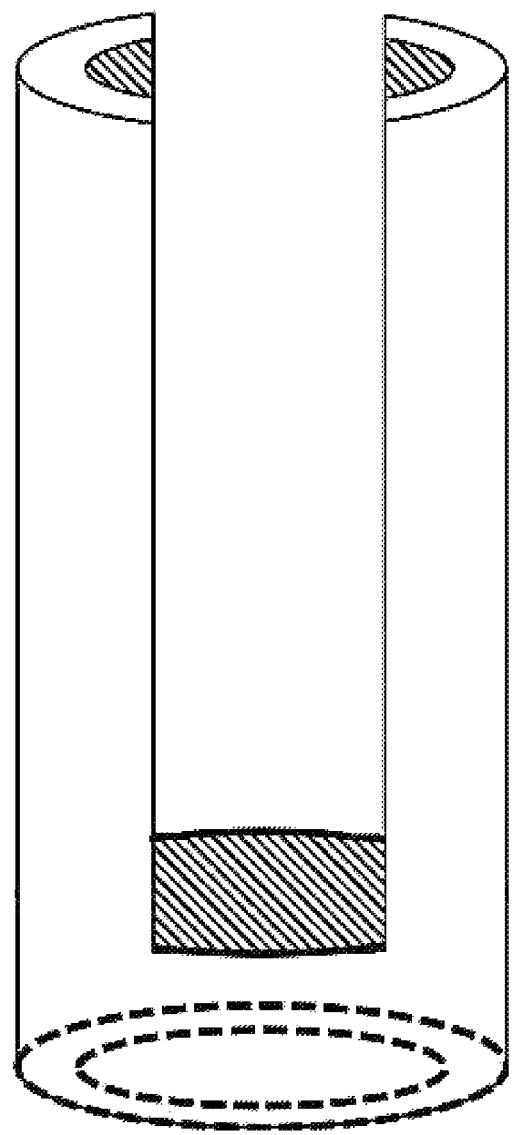
FIG. 7 is a schematic structural view of a sleeving rod.

As shown in FIG. 7, the sleeving rod 4.14 is a cylindrical structure provided with an axial gap and having one end sealed. The bump at one end of each of the disposable fixture member 4.11 and the spring fixture member 4.12 enters the groove 4.9 through the gap of the sleeving rod 4.14. The bump at the other end of the disposable fixture member 4.11 enters the sliding barrel 4.13 through the gap, and contacts the sliding barrel 4.13. The bump at the other end of the spring fixture member 4.12 is flush with the outer surface of the sleeving rod 4.14 through the gap of the sleeving rod 4.14, and located in the sliding barrel 4.13, without contacting the sliding barrel 4.13.

Optionally, the housing 4.3 is divided into an upper portion and a lower portion along an axial direction of the handle 5, and the upper portion and the lower portion are connected and fixed through a fastener.

Figure 8:
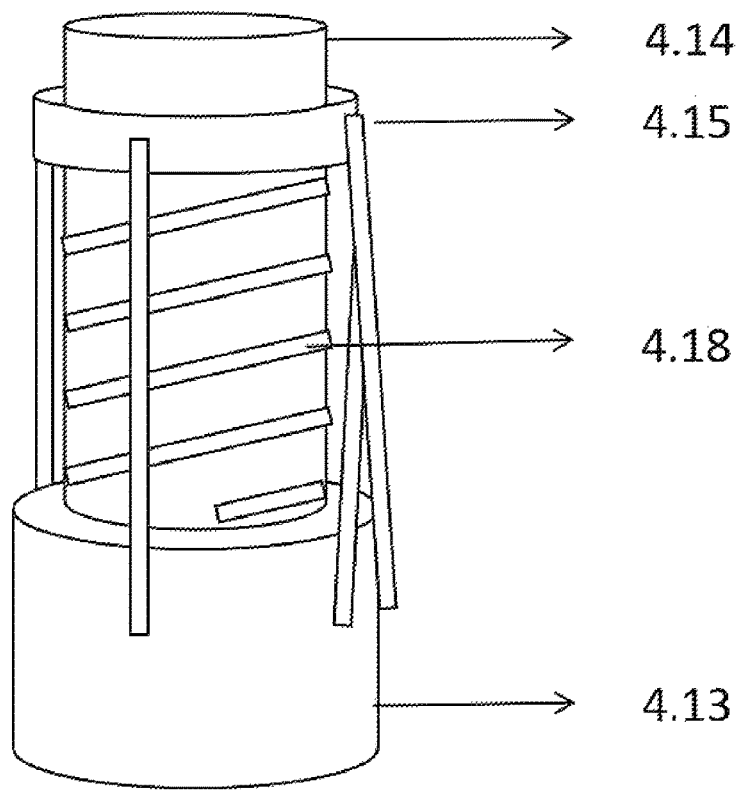
FIG. 8 is a schematic view when a support rod and a distraction rod are collapsed.
Figure 9:
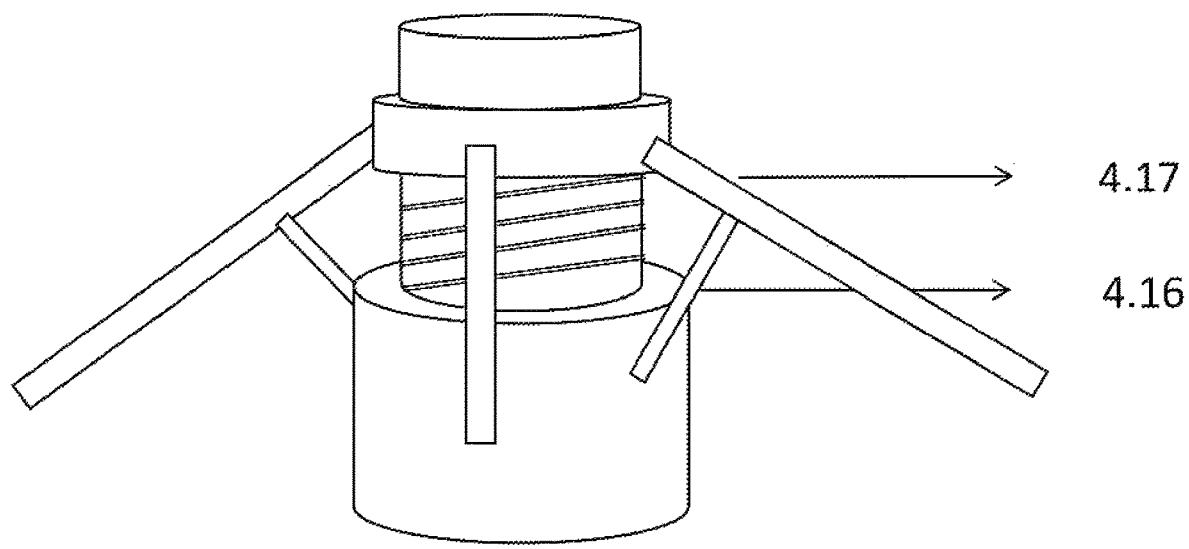
FIG. 9 is a schematic view when a support rod and a distraction rod are expanded.

As shown in FIGS. 8-9, the sliding barrel 4.13 is connected to the fixed hoop 4.15 through the second spring 4.18. The sliding barrel 4.13 and the support rod 4.16, the fixed hoop 4.15 and the distraction rod 4.17, as well as the distraction rod 4.17 and the support rod 4.16 are rotatably connected to each other. Optionally, the sliding barrel 4.13 is connected to the sleeving rod 4.14 through a sliding track. The sliding barrel 4.13 and the support rod 4.16, the fixed hoop 4.15 and the distraction rod 4.17, as well as the distraction rod 4.17 and the support rod 4.16 are hinged to each other.

The device provided by the present disclosure has the following working principle and the following use process:

The X-ray developing particles 3.6 can provide X-rays for positioning during puncture, so as to lay a foundation for X-ray visual puncture. The hydrophilic ultrasound developing coating 3.4 is used in cooperation with an ultrasound machine during puncture to realize real-time developing. Hydrophilic macromolecules interact with water in the blood, which reduces a frictional resistance during puncture and further guides the blood to rise a certain distance in puncture. Without an assistance from other developing devices, a visual prompt on whether the device enters the vessel is given to the medical worker.

Before the puncture, the first spring 4.5 is in the natural state. The second spring 4.18 is in the extended state. The bump at one end of the disposable fixture member 4.11 enters the groove 4.9. The bump at the other end of the disposable fixture member enters the sliding barrel 4.13 through the gap of the sleeving rod 4.14. The sliding barrel 4.13 is fixed by the disposable fixture member 4.11. Both the support rod 4.16 and the distraction rod 4.17 are collapsed.

During the puncture, the sleeving rod 4.14 is held by a hand. The handle 5 and the sleeving rod 4.14 drive the dilation tube 2 to move forward. The device suffers from a resistance from a skin, a tissue and the like. The first spring 4.5 is in a compressed state. The first spring pin 4.7 and the second spring pin 4.8 enter the groove 4.9 to squeeze the disposable fixture member 4.11 and the spring fixture member 4.12. The disposable fixture member 4.11 and the spring fixture member 4.12 are coaxial, and the spring fixture member 4.12 is longer than the disposable fixture member 4.11. On the other hand, the inclination angle of the oblique surface of the first spring pin 4.7 is greater than the inclination angle of the oblique surface of the second spring pin 4.8. Hence, the first spring pin 4.7 contacts the spring fixture member 4.12 first. The spring fixture member 4.12 rotates around the strut. The bump at one end of the spring fixture member 4.12 is withdrawn from the groove 4.9 to enter the push plunger 4.10. The bump at the other end of the spring fixture member enters the sliding barrel 4.13 through the gap of the sleeving rod 4.14. The sliding barrel 4.13 is fixed by the spring fixture member 4.12. The second spring pin 4.8 contacts the disposable fixture member 4.11. The whole disposable fixture member 4.11 slides from the groove 4.9 to enter the push plunger 4.10 and the sleeving rod 4.14. In this case, the second spring 4.18 is still in the extended state. The support rod 4.16 and the distraction rod 4.17 are collapsed.

According to the blood regurgitation preventing puncture guiding device without skin dilation, when the needle tube 1 enters the vessel, since the dilation tube 2 and the sheath 3 are still located outside the vessel, the force does not decrease and the state is unchanged.

After the dilation tube 2 enters the vessel, since the sheath 3 with the larger diameter is still in the tissue, the resistance does not decrease sharply, and the deceleration and stop device 4 keeps a same state as the puncture process.

When the transition section 3.1 of the sheath 3 penetrates through the vessel, the device completely enters the vessel. Obviously, a forward resistance of the device in the vessel is less than a forward resistance of the device in the tissue and a vessel wall. The hydrophilic ultrasound developing coating 3.4 on the surface of the sheath 3 takes a lubricating effect, and the puncture resistance decreases sharply. The first spring 4.5 is extended and restored to the natural state. The first spring pin 4.7 and the second spring pin 4.8 are separated from the grooves 4.9. The disposable fixture member 4.11 is unchanged. Under the spring connected to the handle 5, the spring fixture member 4.12 is restored to a position axially parallel to the sleeving rod 4.14. The sliding barrel 4.13 is not limited. The second spring 4.18 is compressed. The sliding barrel 4.13 is driven to move toward the fixed hoop 4.15 along the sleeving rod 4.14. The support rod 4.16 and the distraction rod 4.17 are expanded. In this case, an outward distraction force is applied to the hand of the medical worker, so as to prompt the medical worker to adjust a needle angle for the puncture.

After the blood regurgitation preventing puncture and guidance device without skin dilation enters a desired site, the seat 3.7 is separated from the connecting post 4.2. The needle tube 1 and the dilation tube 2 are removed at a time. In this case, the valve 3.2 is closed to prevent the blood regurgitation. A catheter with a guidewire is delivered to the sheath 3, with a tip at the valve 3.2. Under a supporting force of the guidewire, the valve 3.2 is opened. The catheter enters the vessel through the transition section 3.1 of the sheath 3. After the catheter is placed to a desired site, the sheath 3 is taken out.

If parts or structural parts fixedly connected to each other are disclosed or involved in the present disclosure, the term "fixedly connected" may be understood as: being detachably and fixedly connected (for example, with a bolt or a screw), and may also be understood as: being non-detachably and fixedly connected (such as riveting and welding), unless otherwise stated. Certainly, the parts fixedly connected to each other may also be of an integral structure, for example, integrally formed by casting (except the parts that cannot be formed integrally).

In addition, unless otherwise stated, terms used to indicate positional relationships or shapes in any technical solution of the present disclosure are intended to include the approximate, similar or close states or shapes. Any part provided by the present disclosure can be assembled by multiple independent components, and may also be an independent part formed integrally.

What is claimed is:

1. A blood regurgitation preventing puncture and guidance device without skin dilation, characterized by comprising a needle tube, a dilation tube, a sheath, a deceleration and stop device, and a handle, wherein the needle tube has an outer diameter of 0.5-2.2 mm, and both the sheath and the dilation tube contain X-ray developing particles;

the dilation tube comprises a connecting seat, a main body section, and a transition section; an inner diameter of the main body section of the dilation tube matches with the needle tube and is 0.03-0.08 mm greater than the outer diameter of the needle tube; the main body section of the dilation tube has a wall thickness of 0.05-1 mm and an axial length of 52-78 mm; the transition section of the dilation tube is connected to the main body section of the dilation tube, and is a tapered structure; along an axial direction of the dilation tube away from the main body section of the dilation tube, an inner diameter, an outer diameter and a wall thickness of the transition section of the dilation tube decrease gradually; the transition section of the dilation tube has an axial length of 8-12 mm; a minimum inner diameter of the transition section of the dilation tube is 0.03-0.08 mm less than the outer diameter of the needle tube; and a position with the minimum inner diameter on the transition section of the dilation tube has a wall thickness of 0.04-0.12 mm;

the sheath comprises a transition section, a valve, a main body section, a hydrophilic ultrasound developing coating, and a seat; the transition section of the sheath is connected to the main body section of the sheath, and is a tapered structure; along an axial direction of the sheath away from the main body section of the sheath, an inner diameter, an outer diameter and a wall thickness of the transition section of the sheath decrease gradually; the transition section of the sheath has an axial length $L_2$ of 3-5 mm; a minimum inner diameter of the transition section of the sheath is 0.03-0.08 mm less than an outer diameter of the main body section of the dilation tube; a position with the minimum inner diameter on the transition section of the sheath has a wall thickness of 0.02-0.08 mm; and the main body section of the sheath has an axial length $L_1$ of 30-75 mm, and a wall thickness of 0.05-0.8 mm;

the deceleration and stop device comprises a dilation tube hole, a connecting post, a housing, spring holes, first springs, spring pin holes, a first spring pin, a second spring pin, grooves, a push plunger, a disposable fixture member, a spring fixture member, a sliding barrel, a sleeving rod, a fixed hoop, a support rod, a distraction rod, and a second spring; the dilation tube hole and two spring pin holes are sequentially formed in the connecting post; the push plunger is provided with the grooves, the spring holes, and holes respectively matching with the disposable fixture member and the spring fixture member; the spring holes are close to an edge of the push plunger, and respectively communicate with the grooves, with a diameter greater than a diameter of the groove; the groove, the spring hole and the spring pin hole are coaxial; the first springs are respectively sleeved on the first spring pin and the second spring pin, and are in a natural state; the first spring comprises one end connected to the spring hole, and the other end connected to the connecting post; the first spring pin and the second spring pin each comprise one end fixedly connected to the spring pin hole, and the other end exposed out of the spring pin hole and contacting the groove; the disposable fixture member and the spring fixture member each are an elongated structure with bumps at two ends; the disposable fixture member and the spring fixture member each are connected to the handle, and comprise one end located in the groove and the other end located in the sliding barrel; the sliding barrel is sleeved on the sleeving rod, and axially and slidably connected to the sleeving rod; the sleeving rod is sequentially in threaded connection with the push plunger and the connecting seat of the dilation tube; the fixed hoop is fixed outside a top of the sleeving rod; the sliding barrel is connected to the fixed hoop through the second spring; the second spring is in an extended state; and the sliding barrel and the support rod, the fixed hoop and the distraction rod, as well as the distraction rod and the support rod are rotatably connected to each other; and the handle penetrates through the sleeving rod, and is in threaded connection with the sleeving rod and the connecting seat of the dilation tube.

2. The blood regurgitation preventing puncture and guidance device without skin dilation according to claim 1, characterized in that the main body section of the sheath and the transition section of the sheath are made of an elastic and rigid material; an outer contour of the transition section of the sheath is tangent to an outer contour of the main body section of the sheath; and an outer contour of the transition section of the dilation tube is tangent to an outer contour of the main body section of the dilation tube.

3. The blood regurgitation preventing puncture and guidance device without skin dilation according to claim 1, characterized in that the valve is located in the transition section of the sheath and close to the main body section, and the valve is made of a material with an elastic modulus of less than 3 MPa.

4. The blood regurgitation preventing puncture and guidance device without skin dilation according to claim 3, characterized in that the valve comprises an elastic membrane and a notch; a diameter of the elastic membrane falls between a diameter of the main body section of the sheath and a diameter of the main body section of the dilation tube; there is one or more notches; the notch passes through a center of the elastic membrane; and a size of the notch falls between the diameter of the elastic membrane and the diameter of the main body section of the dilation tube.

5. The blood regurgitation preventing puncture and guidance device without skin dilation according to claim 1, characterized in that the X-ray developing particles are made of barium sulfate, metal tungsten, metal tantalum or a bismuth-containing compound, and have a size of 1-50 μm; the hydrophilic ultrasound developing coating mainly comprises a hydrophilic polymer and metal particles; and the metal particles are alloy particles or pure metal particles, and have a size of 1-50 μm.

6. The blood regurgitation preventing puncture and guidance device without skin dilation according to claim 1, characterized in that the end of each of the first spring pin and the second spring pin that is exposed out of the spring pin hole is an oblique surface; and an inclination angle of the oblique surface of the first spring pin is greater than an inclination angle of the oblique surface of the second spring pin.

7. The blood regurgitation preventing puncture and guidance device without skin dilation according to claim 1, characterized in that the sleeving rod is a cylindrical structure provided with an axial gap and having one end sealed; the bump at one end of each of the disposable fixture member and the spring fixture member enters the groove through the gap of the sleeving rod; the bump at the other end of the disposable fixture member enters the sliding barrel through the gap; and the bump at the other end of the spring fixture member is flush with an outer surface of the sleeving rod through the gap of the sleeving rod.

8. The blood regurgitation preventing puncture and guidance device without skin dilation according to claim 7, characterized in that the disposable fixture member is unidirectionally and slidably connected to the handle; there is a gap between an elongated portion of the disposable fixture member and the handle; the bump of the disposable fixture member entering the groove matches with the second spring pin in shape; two ends of the spring fixture member are connected to the handle through a spring; the spring is in a natural state; a middle of the spring fixture member is rotatably connected to the handle through a strut; there is a certain gap between the spring fixture member and the handle; and the bump of the spring fixture member entering the groove matches with the first spring pin in shape.

9. The blood regurgitation preventing puncture and guidance device without skin dilation according to claim 8, characterized in that the disposable fixture member and the spring fixture member are opposite around the handle, and are coaxial; a size of the bump of the disposable fixture member entering the groove and a size of the bump of the spring fixture member entering the groove are respectively less than a width of the first spring pin and a width of the second spring pin; and an axial length of the spring fixture member is greater than an axial length of the disposable fixture member.

10. The blood regurgitation preventing puncture and guidance device without skin dilation according to claim 8, characterized in that the strut is deviated from the middle of the spring fixture member, and close to the one end of the spring fixture member with the bump entering the groove.

\* \* \* \* \*